United States Patent
Naya

(10) Patent No.: US 6,992,770 B2
(45) Date of Patent: Jan. 31, 2006

(54) SENSOR UTILIZING ATTENUATED TOTAL REFLECTION

(75) Inventor: Masayuki Naya, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 151 days.

(21) Appl. No.: 10/054,880

(22) Filed: Jan. 25, 2002

(65) Prior Publication Data

US 2002/0126290 A1    Sep. 12, 2002

(30) Foreign Application Priority Data

Jan. 25, 2001 (JP) ............................ 2001-016631
Mar. 27, 2001 (JP) ............................ 2001-089823

(51) Int. Cl.
*G01N 21/55* (2006.01)

(52) U.S. Cl. .................................. 356/445
(58) Field of Classification Search ................ 356/445
See application file for complete search history.

(56) References Cited

U.S. PATENT DOCUMENTS 5,141,311 A * 8/1992 Hickel et al. ............... 356/136
5,416,573 A * 5/1995 Sartor, Jr. .................... 356/71
6,407,804 B1 * 6/2002 Hillmann et al. ............. 356/71
6,752,963 B2 * 6/2004 Dickopf et al. .............. 356/445

FOREIGN PATENT DOCUMENTS

JP        6-167443 A        6/1994

OTHER PUBLICATIONS

Takayuki Okamoto, "Spectral Research" No. 1, pp. 21-23, pp. 26-27, vol. 47.

* cited by examiner

*Primary Examiner*—Richard A. Rosenberger
(74) *Attorney, Agent, or Firm*—Sughrue Mion, PLLC

(57) ABSTRACT

Disclosed herein is a sensor utilizing attenuated total reflection. The sensor includes a first dielectric block; a thin film layer, formed on a first face of the dielectric block, for placing a sample thereon; and a light source for emitting a light beam. The sensor further includes an optical incidence system for collimating the light beam, and making the collimated light beam enter the dielectric block at a predetermined incidence angle so that a condition for total internal reflection is satisfied at an interface between the dielectric block and the thin film layer; a photodetector for detecting the refractive index distribution of the sample obtained within a plane along the interface, by detecting an image carried by the light beam totally reflected at the interface; and an optical compensation system for compensating for image distortion produced by the dielectric block when the predetermined incidence angle of the light beam varies.

43 Claims, 11 Drawing Sheets

F I G . 9
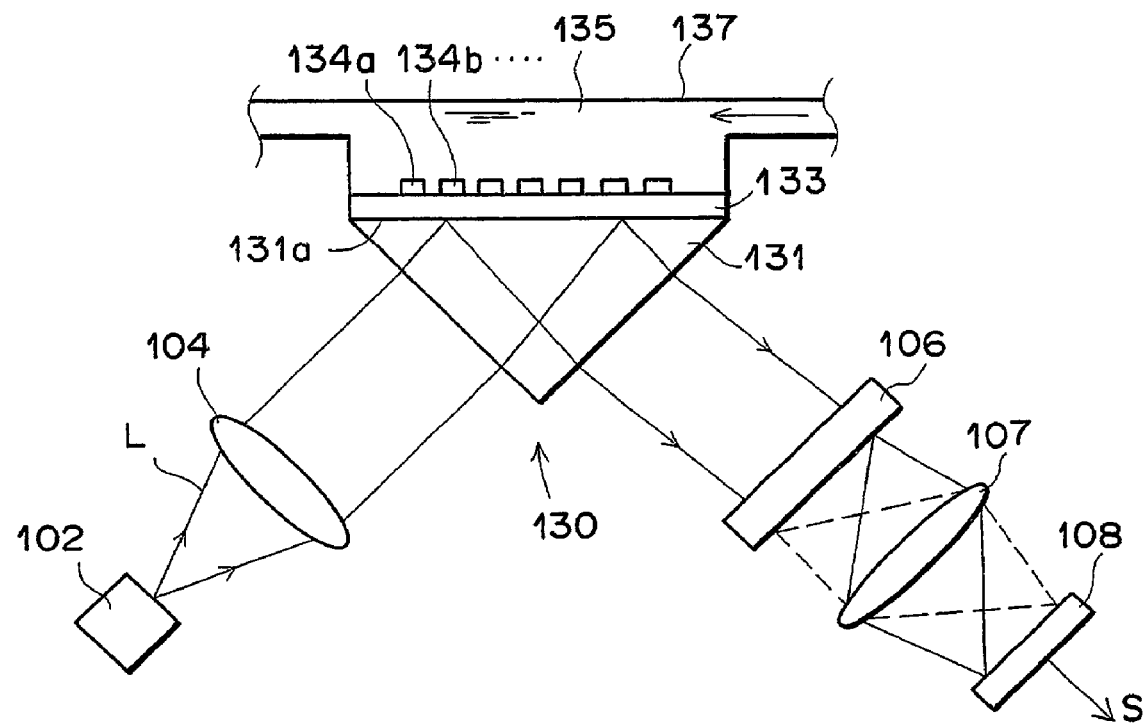

F I G . 10
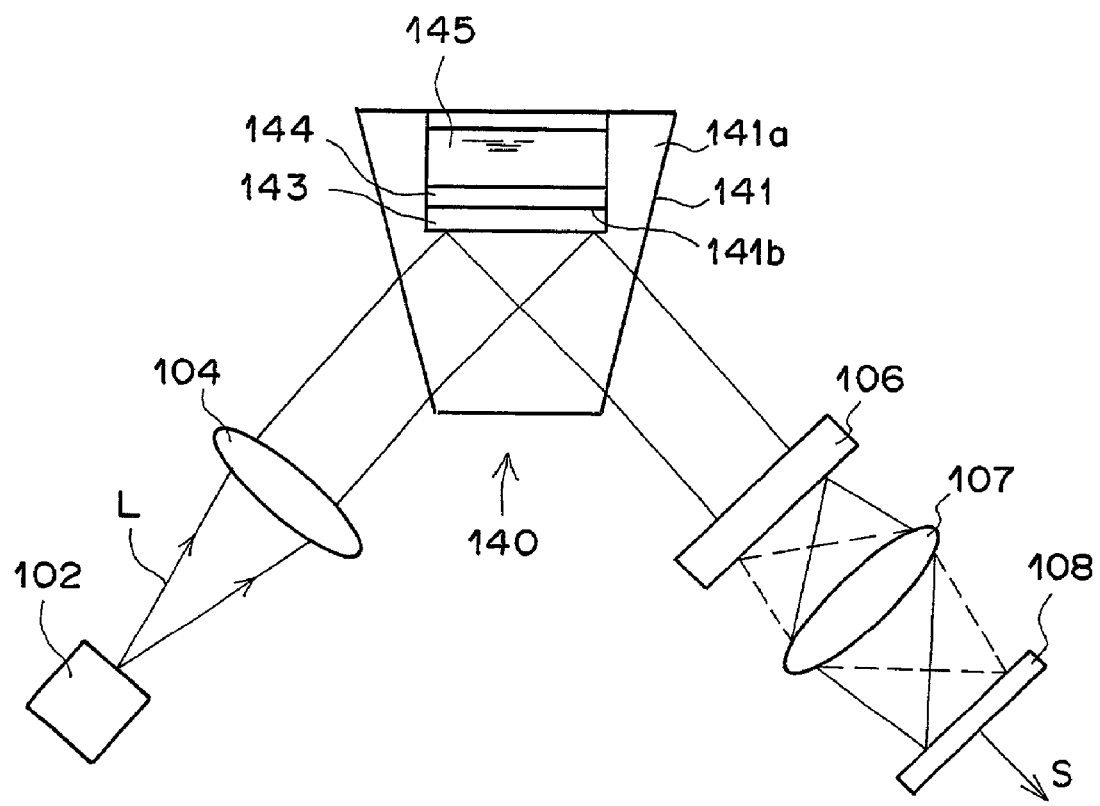

SENSOR UTILIZING ATTENUATED TOTAL REFLECTION

BACKGROUND OF THE INVENTION

1. Field of the Invention

The present invention relates to a sensor utilizing attenuated total reflection (hereinafter referred to as ATR), such as a surface plasmon resonance sensor that detects the refractive index of a sample by utilizing the generation of surface plasmon, and more particularly to a sensor, utilizing ATR, which detects the refractive index distribution of a sample and a sensor, utilizing ATR, which detects a two-dimensional measuring region with a parallel light beam.

2. Description of the Related Art

In metals, if free electrons are caused to vibrate in a group, compression waves called plasma waves will be generated. The compression waves generated in a metal surface are quantized and called surface plasmon.

A wide variety of surface plasmon resonance sensors have been proposed to quantitatively analyze a substance in a sample by taking advantage of a phenomenon that surface plasmon is excited by light waves. Among such sensors, one employing a system called "Kretschmann configuration" is particularly well known (e.g., see Japanese Unexamined Patent Publication No. 6(1994)-167443).

The surface plasmon resonance sensor employing the aforementioned system is equipped with a dielectric block formed, for example, into the shape of a prism; a metal film, formed on a face of the dielectric block, for placing a sample thereon; and a light source for emitting a light beam. The sensor is further equipped with an optical system for making the light beam enter the dielectric block so that a condition for total internal reflection is satisfied at the interface between the dielectric block and the metal film and that various angles of incidence, including a surface plasmon resonance condition, are obtained; and photodetection means for measuring the intensity of the light beam totally reflected at the interface, and detecting the state of surface plasmon resonance.

In the surface plasmon resonance sensor mentioned above, if a light beam strikes the metal film at a specific incidence angle $\theta_{sp}$ equal to or greater than a critical angle of incidence at which total internal reflection takes place, evanescent waves with an electric field distribution are generated in a sample in contact with the metal film, whereby a surface plasmon is excited at the interface between the metal film and the sample. When the wave vector of the evanescent light is equal to the wave number of the surface plasmon and therefore the wave numbers between the two are matched, the evanescent waves and the surface plasmon resonate and light energy is transferred to the surface plasmon, whereby the intensity of the light totally reflected at the interface between the dielectric block and the metal film drops sharply. The sharp intensity drop (i.e., ATR) is generally detected as a dark line by the above-mentioned photodetection means. The relationship between the incidence angle $\theta$ of a light beam with respect to the interface and the intensity I of the light beam totally reflected at the interface is shown in FIG. 2. In the figure, the specific incidence angle $\theta_{sp}$ indicates an incidence angle at which ATR occurs.

Note that the above-mentioned resonance occurs only when the incident light beam is a p-polarized light beam. Therefore, in order to make the resonance occur, it is necessary that a light beam be p-polarized before it strikes the interface.

If the wave number of the surface plasmon is found from the specific incidence angle $\theta_{sp}$ at which ATR takes place, the dielectric constant of a sample can be calculated by the following Equation:

$$K_{SP}(\omega) = \frac{\omega}{c} \sqrt{\frac{\varepsilon_m(\omega)\varepsilon_s}{\varepsilon_m(\omega) + \varepsilon_s}}$$

where $K_{sp}$ represents the wave number of the surface plasmon, $\omega$ represents the angular frequency of the surface plasmon, c represents the speed of light in vacuum, and $\varepsilon_m$ and $\varepsilon_s$ represent the dielectric constants of the metal and the sample, respectively.

If the dielectric constant $\varepsilon_s$ of a sample is found, the density of a specific substance in the sample is found based on a predetermined calibration curve, etc. As a result, a specific substance in the sample can be quantitatively analyzed by finding the specific incidence angle $\theta_{sp}$ at which the intensity of the reflected light drops sharply.

In addition, a leaky mode sensor is known as a similar sensor making use of ATR, as disclosed, for instance, in "Spectral Research," Vol. 47, No.1 (1998), pp. 21 to 23 and pp. 26 to 27. The leaky mode sensor is equipped with a dielectric block formed, for example, into the shape of a prism; a cladding layer formed on a face of the dielectric block; and an optical waveguide layer, formed on the cladding layer, for placing a sample thereon. The leaky mode sensor is further equipped with a light source for emitting a light beam; an optical system for making the light beam enter the dielectric block at various angles of incidence so that a condition for total internal reflection is satisfied at the interface between the dielectric block and the cladding layer and so that ATR occurs by the excitation of a waveguide mode in the optical waveguide layer; and a photodetection means for measuring the intensity of the light beam totally reflected at the interface between the dielectric block and the cladding layer, and detecting the excited state of the waveguide mode, that is, the state of ATR.

In the leaky mode sensor with the construction mentioned above, if a light beam strikes the cladding layer through the dielectric block at angles of incidence equal to or greater than an angle of incidence at which total internal reflection takes place, the light beam is transmitted through the cladding layer and then only light with a specific wave number, incident at a specific incidence angle, propagates through the optical waveguide layer in a waveguide mode. If the waveguide mode is excited in this manner, the greater part of the incident light is confined within the optical waveguide layer, and consequently, ATR occurs in which the intensity of light totally reflected at the above-mentioned interface drops sharply. Since the wave number of light propagating in the optical waveguide layer depends on the refractive index of a sample on the optical waveguide layer, the refractive index of the sample and the properties of the sample related to the refractive index thereof can be analyzed by finding the above-mentioned specific incidence angle $\theta_{sp}$ at which ATR takes place.

In addition, the above-mentioned surface plasmon resonance sensors or leaky mode sensors can be used to measure the refractive index distribution, within a plane along the aforementioned interface, of a sample. In the case of the surface plasmon resonance sensors, the relationship between the incidence angle of a light beam with respect to the interface and the intensity of the light beam totally reflected at the interface is shown in FIG. 2. The specific incidence angle $\theta_{sp}$ shown in FIG. 2 indicates an angle at which ATR occurs. The aforementioned relationship between the incidence angle and the light intensity will be shifted in the horizontal direction of FIG. 2, if the refractive index of a sample varies. Therefore, if a light beam strikes the aforementioned interface at an incidence angle near the specific incidence angle $\theta_{sp}$, the intensity of the light beam totally reflected at the interface varies with the refractive index of a sample. Hence, if a parallel light beam with a relatively wide beam section is caused to strike the interface, and an image carried by the parallel light beam totally reflected at the interface (i.e., intensity distribution within the beam section) is detected, the refractive index distribution of a sample within a plane along the interface can be detected.

The foregoing description of the surface plasmon resonance sensors applies to the leaky mode sensors, because the leaky mode sensors differ from the surface plasmon resonance sensors only in that total internal reflection is attenuated by the excitation of a waveguide mode in the waveguide layer instead of being attenuated by surface plasmon resonance. Therefore, it is also possible to detect the refractive index distribution of a sample by employing the leaky mode sensors.

In analyzing physical properties by the aforementioned surface plasmon sensors or leaky mode sensors, there are cases where a plurality of samples need to be measured under the same condition, or cases where the two-dimensional physical property information of a sample is needed. In such cases, the aforementioned surface plasmon sensors or leaky mode sensors can be utilized.

For instance, a description will be given of how the two-dimensional physical properties of a sample are analyzed by the surface plasmon resonance sensors. The relationship between the incidence angle of a light beam with respect to an interface and the intensity of the light beam totally reflected at the interface, as previously stated, is shown in FIG. 2. The specific incidence angle $\theta_{sp}$ indicates an angle at which ATR occurs. This relationship will be horizontally shifted if the refractive index of a substance on a metal film varies. Therefore, if a light beam strikes a two-dimensional region on the interface at a predetermined incidence angle, a portion of the region where ATR occurs at the incidence angle, that is, a light component incident on a point on the interface where a specific substance is present on the metal film, is detected as a dark line. Hence, if parallel light with a relatively wide cross section is employed and the light intensity distribution of the cross section of the light beam totally reflected at the interface is detected, the distribution of specific substances within a plane along the interface can be measured. Since the intensity of the reflected light is reduced at angles above and below the predetermined incidence angle $\theta_{sp}$, as shown in FIG. 2, the light intensity distribution of the cross section of the light beam, incident on the interface at predetermined angles and reflected, indicates the two-dimensional refractive distribution of a substance (sample) present on the metal film.

The foregoing description of the surface plasmon resonance sensors applies to the leaky mode sensors, because the leaky mode sensors differ from the surface plasmon resonance sensors only in that total internal reflection is attenuated by the excitation of a waveguide mode in the waveguide layer instead of being attenuated by surface plasmon resonance. Therefore, it is also possible to detect the two-dimensional physical properties of a sample by employing the leaky mode sensors.

However, in the conventional sensor utilizing ATR, which is constructed to detect the refractive index distribution of a sample in the aforementioned manner, there are cases where the image by totally reflected light is distorted and therefore the refractive index distribution cannot be accurately measured.

On the other hand, in the sensor utilizing ATR, in which a parallel light beam is caused to strike an interface to detect the light intensity distribution of the cross section of reflected light, there are cases where a laser light is employed and, because of this, the light intensity distribution of a light beam detected by photodetection means (two-dimensional sensor) cannot be accurately measured due to coherent noise caused by the laser light beam. Particularly, in the case of a charge-coupled device (CCD) sensor being employed as a two-dimensional image sensor, there are cases where multiple interferences due to coherent noise take place within a protective film usually provided on the light-receiving face of the CCD sensor and therefore interference stripes occur on an image plane. Thus, there is a great influence due to coherent noise.

SUMMARY OF THE INVENTION

The present invention has been made in view of the circumstances mentioned above. Accordingly, it is an object of the present invention to provide a planar type sensor, utilizing ATR, which is capable of measuring the refractive index distribution of a sample with a high degree of accuracy, while eliminating image distortion due to totally reflected light. Another object of the present invention is to provide a sensor, utilizing ATR, which is capable of making an accurate measurement, even when making a laser light beam strike an interface as a parallel light beam having a cross section of considerable size and then detecting the reflected light beam.

To achieve the objects of the present invention mentioned above, there is provided a first sensor utilizing attenuated total reflection. The first sensor comprises a first dielectric block; a thin film layer, formed on a first face of the dielectric block, for placing a sample thereon; a light source for emitting a light beam; an optical incidence system for collimating the light beam, and making the collimated light beam enter the dielectric block at a predetermined incidence angle so that a condition for total internal reflection is satisfied at an interface between the dielectric block and the thin film layer; photodetection means for detecting the refractive index distribution of the sample that is obtained within a plane along the interface, by detecting an image carried by the light beam totally reflected at the interface; wherein an optical compensation system for compensating for image distortion which is produced by the dielectric block when the predetermined incidence angle of the light beam varies is provided.

In accordance with the present invention, there is provided a second sensor utilizing attenuated total reflection that occurs due to surface plasmon resonance. The second sensor is constructed as the aforementioned surface plasmon sensor, and comprises a first dielectric block; a thin film layer comprising a metal film, formed on a first face of the dielectric block, for placing a sample thereon; a light source for emitting a light beam; an optical incidence system for collimating the light beam, and making the collimated light beam enter the dielectric block at a predetermined incidence angle so that a condition for total internal reflection is satisfied at an interface between the dielectric block and the thin film layer; photodetection means for detecting the refractive index distribution of the sample that is obtained within a plane along the interface, by detecting an image carried by the light beam totally reflected at the interface; wherein an optical compensation system for compensating for image distortion which is produced by the dielectric block when the predetermined incidence angle of the light beam varies is provided.

In accordance with the present invention, there is provided a third sensor utilizing attenuated total reflection that occurs when a waveguide mode in an optical waveguide layer is excited. The third sensor is constructed as the aforementioned leaky mode sensor, and comprises a first dielectric block; a thin film layer comprising (1) a cladding layer formed on a first face of the dielectric block and (2) the optical waveguide layer formed on the cladding layer; a light source for emitting a light beam; an optical incidence system for collimating the light beam, and making the collimated light beam enter the dielectric block at a predetermined incidence angle so that a condition for total internal reflection is satisfied at an interface between the dielectric block and the cladding layer; photodetection means for detecting the refractive index distribution of the sample that is obtained within a plane along the interface, by detecting an image carried by the light beam totally reflected at the interface; wherein an optical compensation system for compensating for image distortion which is produced by the dielectric block when the predetermined incidence angle of the light beam varies is provided.

In the aforementioned sensors, the above-mentioned optical compensation system can be constructed of a second dielectric block for compensation and a screen for image observation. The second dielectric block has the same section as that of the first dielectric block within an incidence plane (including both a line normal to the interface and a line normal to the wavefront of the light beam) of the light beam with respect to the interface, and is formed from a material of the same refractive index as the first dielectric block. The second dielectric block is disposed so that it receives the light beam emerging from the first dielectric block. The screen for image observation is formed on a face of the second dielectric block that corresponds to the first face of the first dielectric block. The screen can be formed, for example, from diffusers or phosphors.

The above-mentioned first dielectric block can be formed as a single block having the first face on which the thin film layer is formed, a second face that the light beam enters, and a third face from which the light beam emerges. In that case, the second dielectric block for compensation is likewise constructed.

In addition, the first dielectric block may comprise a first portion having a second face that the light beam enters and a third face from which the light beam emerges, and a second portion having the first face on which the thin film layer is formed. The first portion and the second portion are joined together through index-matching means. In that case, the second dielectric block for compensation is constructed the same way as the first dielectric block.

According to investigations made by the inventors, the reason that distortion occurs in an image carried by totally reflected light in conventional surface-type sensors utilizing ATR is that the traveling angle of the totally reflected light traveling through the dielectric block differs from the traveling angle of the light incident on the detecting face of photodetection means. Even if the angle of installation of the photodetection means is adjusted so that the image distortion is eliminated, an image on the detecting face of the photodetection means will be distorted, if the angle of incidence of the measuring light varies. A variation in the angle of incidence always occurs when the angle of incidence of the measuring light is scanned, for example when a substance having a different incidence angle condition for ATR is measured.

The sensor of the present invention utilizing ATR is provided with an optical compensation system for compensating for image distortion that occurs when the incidence angle of a light beam with respect to the interface between the dielectric block and the thin film layer varies. With this compensation system, image distortion is eliminated and the refractive index distribution of a sample can be measured with a high degree of accuracy.

To prevent a reduction in accuracy of measurement due to coherent noise and in accordance with the present invention, there is provided a fourth sensor utilizing attenuated total reflection, which comprises a light source for emitting a light beam; a measuring unit comprising (1) a dielectric block transparent to the light beam, (2) a thin film layer formed on a first face of the dielectric block, and (3) a sample holding mechanism for holing a sample on the thin film layer; an optical incidence system for collimating the light beam so that the light beam has a cross section of considerable size, and making the collimated light beam enter the dielectric block at a predetermined incidence angle so that a condition for total internal reflection is satisfied at an interface between the dielectric block and the thin film layer; a screen, disposed in an optical path of the collimated light beam totally reflected at the interface, for converting light intensity distribution in the cross section of the collimated light beam into a visual image; a two-dimensional sensor on which the visual image on the screen is formed; and an optical image-forming system for forming the visual image on the screen onto the two-dimensional sensor.

In accordance with the present invention, there is provided a fifth sensor utilizing attenuated total reflection that occurs due to surface plasmon resonance. The fifth sensor is constructed as the aforementioned surface plasmon sensor, and comprises a light source for emitting a light beam; a measuring unit comprising (1) a dielectric block transparent to the light beam, (2) a thin film layer comprising a metal film, formed on a first face of the dielectric block, and (3) a sample holding mechanism for holing a sample on the thin film layer; an optical incidence system for collimating the light beam so that the light beam has a cross section of considerable size, and making the collimated light beam enter the dielectric block at a predetermined incidence angle so that a condition for total internal reflection is satisfied at an interface between the dielectric block and the thin film layer; a screen, disposed in an optical path of the collimated light beam totally reflected at the interface, for converting light intensity distribution in the cross section of the collimated light beam into a visual image; a two-dimensional sensor on which the visual image on the screen is formed; and an optical image-forming system for forming the visual image on the screen onto the two-dimensional sensor.

In accordance with the present invention, there is provided a sixth sensor utilizing attenuated total reflection that occurs when a waveguide mode in an optical waveguide layer is excited. The sixth sensor is constructed as the aforementioned leaky mode sensor, and comprises a light source for emitting a light beam; a measuring unit comprising (1) a dielectric block transparent to the light beam, (2) a thin film layer comprising a cladding layer formed on a first face of the dielectric block, and the optical waveguide layer formed on the cladding layer, and (3) a sample holding mechanism for holing a sample on the thin film layer; an optical incidence system for collimating the light beam so that the light beam has a cross section of considerable size, and making the collimated light beam enter the dielectric block at a predetermined incidence angle so that a condition for total internal reflection is satisfied at an interface between the dielectric block and the thin film layer; a screen, disposed in an optical path of the collimated light beam totally reflected at the interface, for converting light intensity distribution in the cross section of the collimated light beam into a visual image; a two-dimensional sensor on which the visual image on the screen is formed; and an optical image-forming system for forming the visual image on the screen onto the two-dimensional sensor.

In the sensors utilizing attenuated total reflection, the expression "cross section of considerable size" refers to a cross section of the size needed for a collimated light beam to strike a desired measurement region on the interface.

In the sensors of the present invention, the aforementioned screen may comprise a diffusing plate or fluorescent plate. The fluorescent plate may employ, for example, a substrate coated with a fluorescent material.

In the fourth through the sixth sensors of the present invention, a sensing medium that interacts with a specific component in the sample may be disposed on the thin film layer. In addition, a plurality of sensing media of the same or different kinds maybe disposed on different points on the thin film layer. In the case of a plurality of sensing media, the expression "cross section of considerable size" means a cross section capable of irradiating a light beam to a plurality of sensing media at the same time.

In the fourth through the sixth sensors of the present invention, the aforementioned sample holding mechanism is employed to hold a sample on a thin film layer and may be formed into the shape of a container having a sample-holding portion for holding a liquid sample. The sample holding mechanism may be provided with a passage through which a liquid sample passes while contacting the sensing medium.

In the fourth through the sixth sensors of the present invention, the aforementioned dielectric block may comprise a first portion having a second face that the light beam enters and a third face from which the light beam emerges, and a second portion formed separately from the first portion and having the first face on which the thin film layer is formed. The second portion and the sample holding mechanism may be formed integrally with each other, and the second portion may be joined with the first portion through index-matching means. The second portion and the sample holding mechanism, integrally formed with each other, are exchangeable with respect to the first portion.

In addition, the dielectric block, thin film layer, and sample holding mechanism of the measuring unit may be formed integrally with one another.

In the aforementioned sensors of the present invention utilizing ATR, a collimated light beam with a cross section of considerable size strikes the interface. An image carried by the light beam reflected at the interface is visually formed onto a screen and is diffused. After diffusion, the image is formed onto a two-dimensional sensor. Because of this, the present invention is capable of eliminating coherent noise that occurs when a laser light beam is employed, and making an accurate measurement. Thus, the present invention is capable of making a measurement of the two-dimensional physical property information of a sample and a simultaneous measurement of samples with a high degree of accuracy.

In the case where a sensing medium that interacts with a specific component in a sample is disposed on a thin film layer, and the sample holding mechanism is provided with a passage through which a liquid sample passes while contacting the sensing medium, the density of the sample can be kept constant even when the specific component gradually reacts with the sensing medium, because the liquid sample is passing through the passage during measurement. In addition, if a plurality of sensing media are disposed on different positions on the thin film layer, different specific substances in the sample that interact with the sensing media can be simultaneously detected and measurement efficiency can be enhanced.

BRIEF DESCRIPTION OF THE DRAWINGS

The present invention will be described in further detail with reference to the accompanying drawings wherein:

FIG. 9 is a side view showing a surface plasmon resonance sensor constructed according to an eighth embodiment of the present invention;

FIG. 10 is a side view showing a surface plasmon resonance sensor constructed according to a ninth embodiment of the present invention.

DESCRIPTION OF THE PREFERRED EMBODIMENTS

Figure 1:
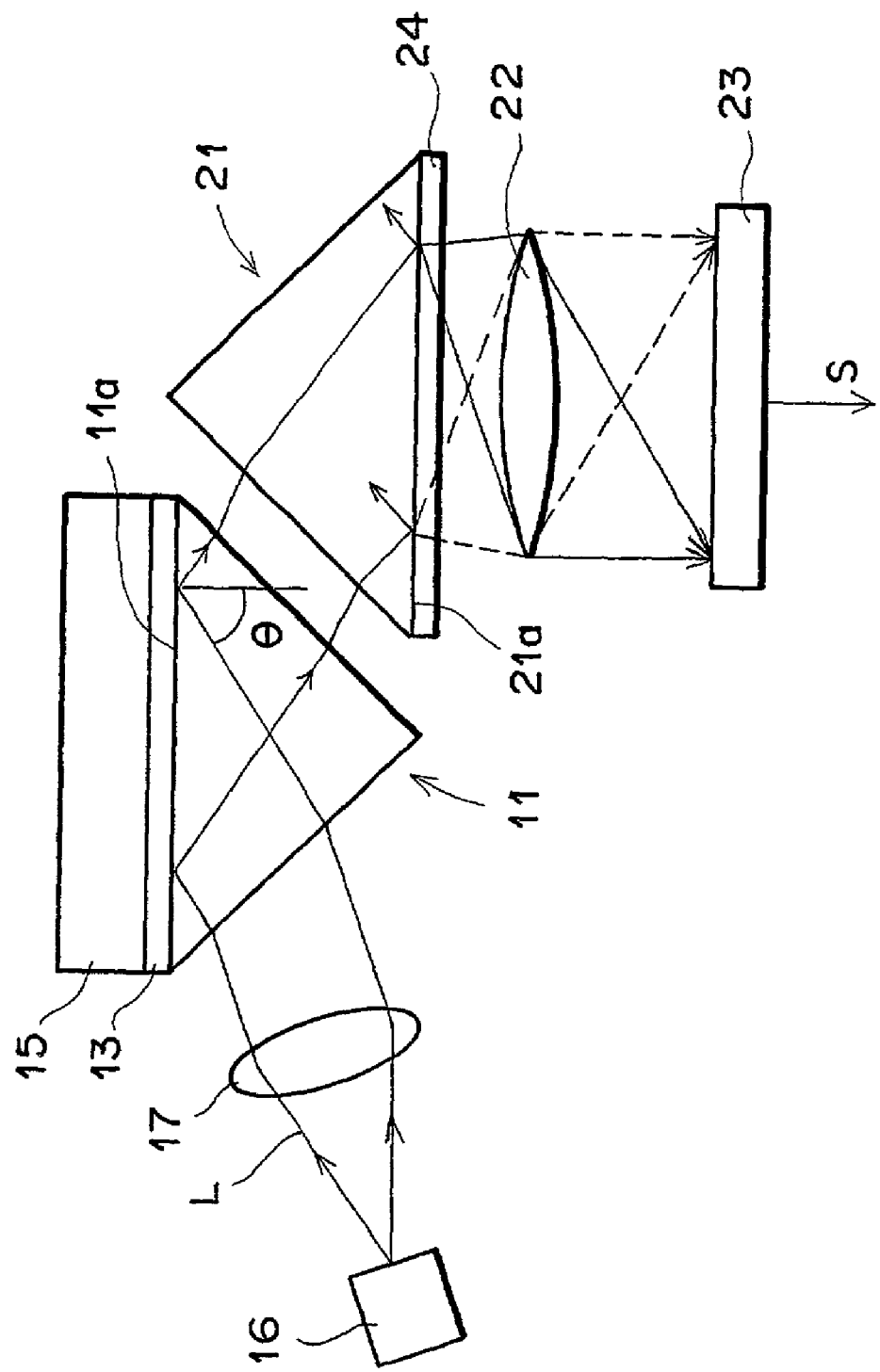
FIG. 1 is a side view showing a surface plasmon resonance sensor constructed according to a first embodiment of the present invention.

Referring now in greater detail to the drawings and initially to FIG. 1, there is shown a sensor utilizing ATR, in accordance with a first embodiment of the present invention.

The sensor of the first embodiment is formed as the aforementioned surface plasmon resonance sensor. As shown in FIG. 1, the sensor has a transparent dielectric block 11 and a metal film 13. The dielectric block 11 is formed from synthetic resin such as polymethylmethacrylate (PMMA), etc., or optical glass such as BK7, etc., and is formed, for example, into the shape of a trigonal prism. The metal film 13 is formed, for example, from gold, silver, copper, aluminum, etc., and is mounted on the top face of the dielectric block 11. A sample 15 to be analyzed is disposed on the metal film 13.

The sensor is further provided with a laser light source 16 for emitting a light beam L; a collimator lens 17 for collimating the light beam L emitted divergently from the laser light source 16; a compensating prism 21 for compensating for image distortion to be described later; an image forming lens 22; and a CCD area sensor (photodetection means) 23. In addition, the bottom surface 21a of the compensating prism 21 is provided with a diffusing film 24 that constitutes a screen for observing an image.

Operation of the surface plasmon resonance sensor will hereinafter be described. The light beam L emitted from the laser light source 16 is collimated by the collimator lens 17. The collimated light beam L enters the dielectric prism 11 and strikes an interface 11a between the dielectric prism 11 and the metal film 13. The incidence angle θ of the light beam L with respect to the interface 11a is set so that a condition for total internal reflection is satisfied at the interface 11a and so that surface plasmon resonance is able to occur.

In the first embodiment, the collimator lens 17 constitutes an optical incidence system. In addition, it is necessary that the light beam L be p-polarized before it strikes the interface 11a. For this reason, the laser light source 16 is disposed so that the polarization direction thereof becomes a predetermined direction. Alternatively, the polarization direction of the light beam L may be controlled with a wavelength plate, a polarizing plate, etc.

The light beam L incident on the interface 11a is totally reflected there. The totally reflected light beam L emerges from the dielectric prism 11. The light beam L emerging from the dielectric prism 11 enters the compensating prism 21 and is totally reflected at the interface between the compensating prism 21 and the diffusing film 24. When this is occurring, evanescent light propagating from the interface between the compensating prism 21 and the diffusing film 24 is diffused by the diffusing film 24. An image, carried by the light beam L, is formed onto the diffusing film 24. This image is formed on the image pick-up face of the CCD area sensor 23 by the image forming lens 22.

Figure 2:
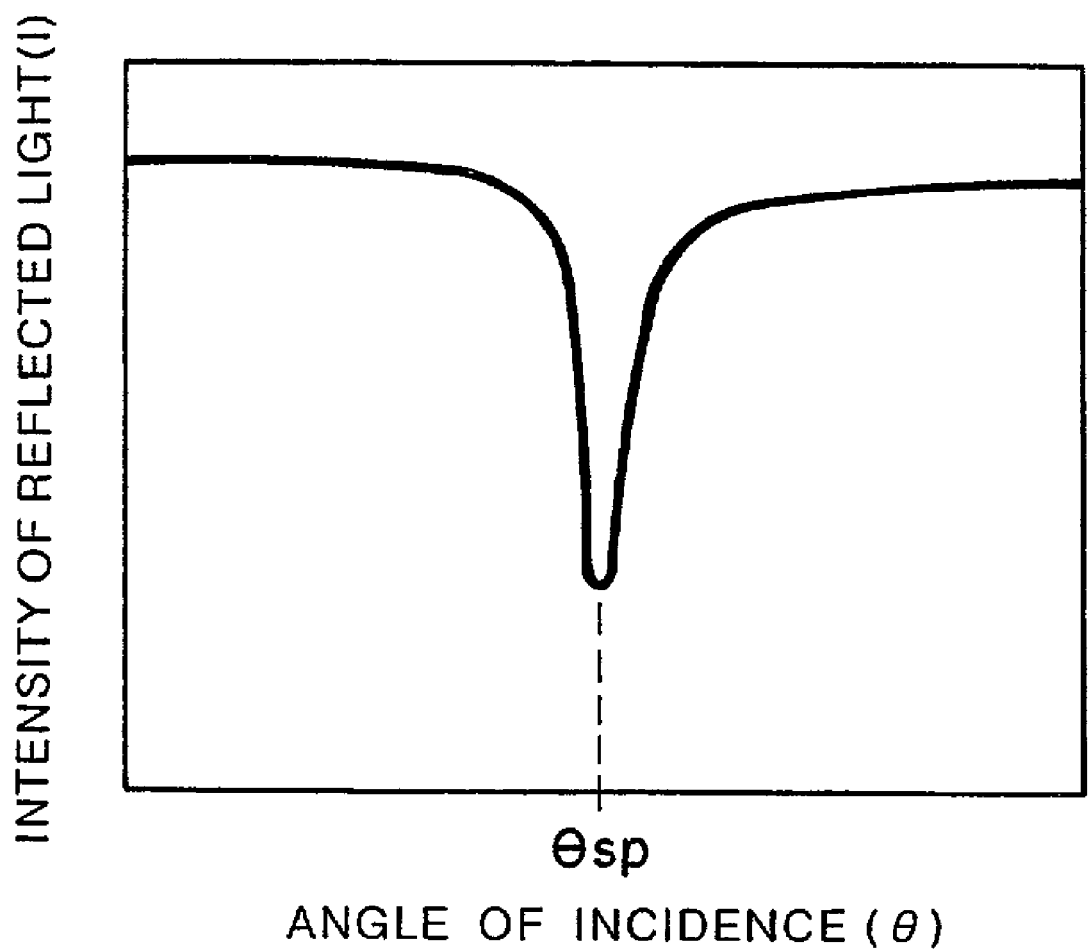
FIG. 2 is a graph showing the relationship between the incidence angle of a light beam with respect to an interface and the intensity of the light beam totally reflected at the interface, obtained according to the surface plasmon resonance sensor shown in FIG. 1.

When the light beam L is totally reflected at the interface 11a, as described above, evanescent waves propagate from the interface 11a to the side of the metal film 13. In the case where the light beam L strikes the interface 11a at a specific incidence angle $\theta_{sp}$, the evanescent waves resonate with the surface plasmon excited at the surface of the metal film 13, and consequently, the intensity I of the reflected light is sharply attenuated. The relationship between the incidence angle θ of the light beam L with respect to the interface 11a and the intensity of the light totally reflected at the interface 11a is shown in FIG. 2. In the figure, the incidence angle $\theta_{sp}$ represents an angle at which ATR occurs.

This relationship will be shifted in the horizontal direction of FIG. 2, if the refractive index of the sample 15 varies. Therefore, the intensity of the totally reflected light beam L varies with the refractive index of the sample 15. Hence, the image formed by the diffusing film 24 and picked up by the CCD area sensor 23, that is, the intensity distribution, within the beam cross section, of the totally reflected light beam L represents the refractive index distribution of the sample 15 within a plane along the interface 11a.

Therefore, if an image signal S output from the CCD area sensor 23 is input to an image display means such as a CRT display, a liquid crystal display panel, etc., and an image carried by the image signal S is reproduced and displayed, the refractive index distribution of the sample can be observed. In addition, if the image signal S is input to an optical scanning-recording unit, etc., an image carried by the image signal S can be reproduced as a hard copy. Note that instead of the diffusing film 24, a diffusing plate or fluorescent screen may be disposed for observation of an image carried by the light beam L.

As described previously, if the incidence angle θ of the light beam L with respect to the interface 11a varies, the optical path of the light beam L within the dielectric prism 11 varies and therefore distortion of ten occurs in an image carried by the light beam L totally reflected at the interface 11a. A description will be given of how the image distortion is eliminated.

The second dielectric prism 21 for compensation is formed from the same material as the first dielectric prism 11 and has the same sectional shape as that of the first dielectric prism 11 within the incidence plane (including both a line normal to the interface 11a and a line normal to the wavefront of the light beam L) of the light beam L with respect to the interface 11a. The second dielectric prism 21 is disposed so that the light beam L emerging from the first dielectric prism 11 enters along the same optical path as the optical path along which the light beam L enters the first dielectric prism 11. If the second dielectric prism 21 is thus disposed, compensation for image distortion due to a variation in the optical path can be made. That is, an image that the light beam L carries at the surface 21a of the second dielectric prism 21 (which corresponds to the interface 11a of the first dielectric prism 11) does not contain image distortion due to a variation in the optical path.

Thus, if an image formed on the diffusing film 24 on the prism surface 21a is picked up by the CCD area sensor 23 and is utilized, the refractive index distribution can be accurately measured.

Figure 3:
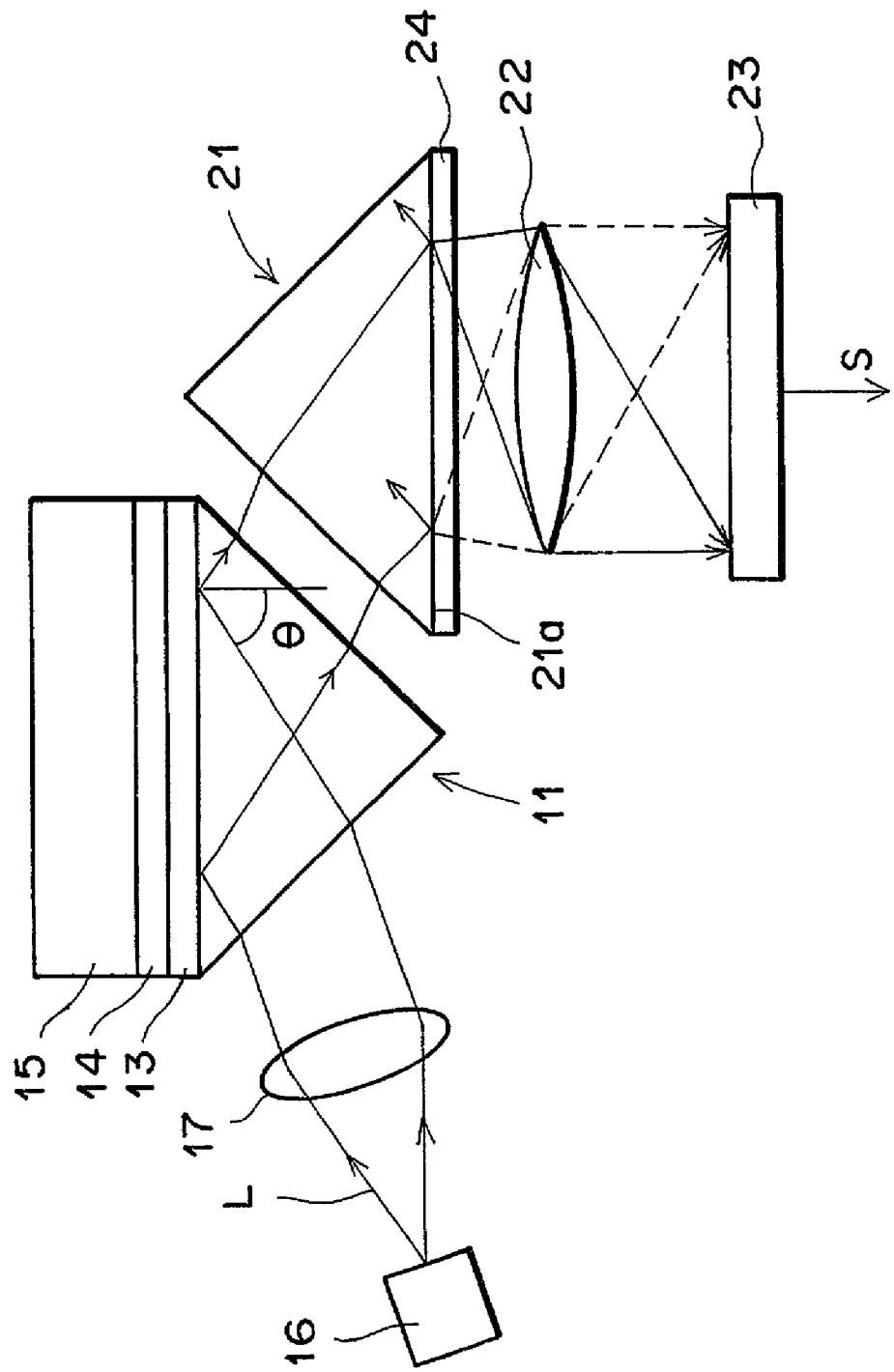
FIG. 3 is a side view showing a surface plasmon resonance sensor constructed according to a second embodiment of the present invention.

FIG. 3 shows a second embodiment of the present invention utilizing ATR. Note in the figure that the same reference numerals are applied to the same parts as those in FIG. 1, and that a description thereof will not be given unless particularly necessary (the same applies to all of the following descriptions).

The second embodiment utilizing ATR is also formed as the aforementioned surface plasmon resonance sensor. The sensor of the second embodiment differs from the sensor shown in FIG. 1 in that a sensing medium 14 is mounted on a first dielectric prism 11 and that a sample 15 to be analyzed is placed on the sensing medium 14. The remaining points are constructed the same way as the sensor of FIG. 1.

The sensing medium 14 couples with a specific substance in the sample 15. As a combination of the specific substance and the sensing medium 14, there is, for example, a combination of an antigen and an antibody.

In the second embodiment, the refractive index of the sensing medium 14 varies with the coupled state between a specific substance in the sample 15 and the sensing medium 14. Hence, if an image formed on a prism surface 21a by a diffusing film 24 is picked up by a CCD area sensor 23, and the image is utilized, the refractive index distribution of the sensing medium 14 can be obtained. That is, the distribution of the coupled states between a specific substance in the sample 15 and the sensing medium 14 can be obtained. In this case, the sample 15 and the sensing medium 14 become samples that are analyzed by the second embodiment. The second embodiment, as with the first embodiment, is provided with a second dielectric prism 21 for compensation. Therefore, the second embodiment, as with the first embodiment, is capable of eliminating image distortion that occurs as the incidence angle θ of the light beam L with respect to the interface 11a varies.

Figure 4:
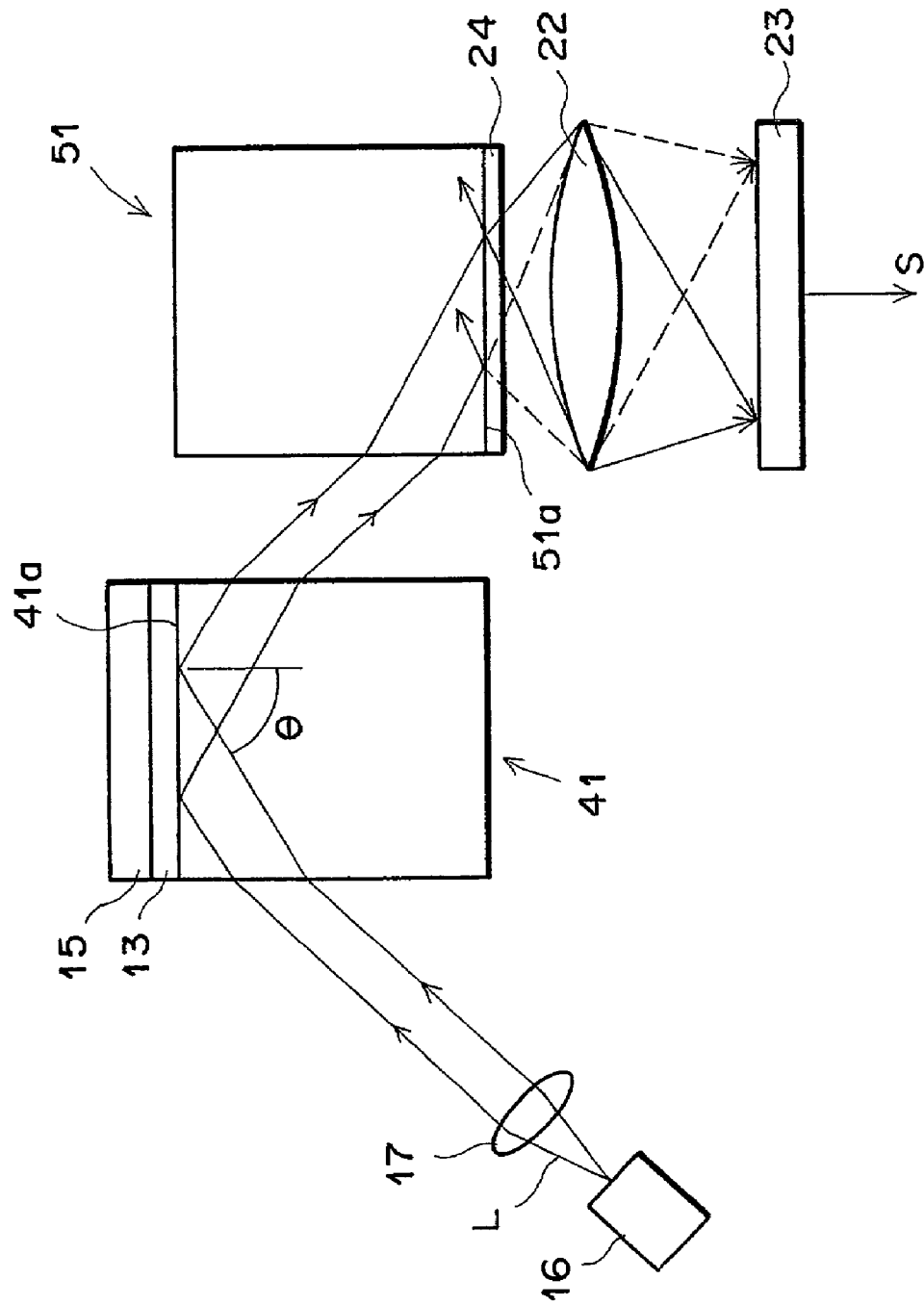
FIG. 4 is a side view showing a surface plasmon resonance sensor constructed according to a third embodiment of the present invention.

FIG. 4 shows a third embodiment of the present invention utilizing ATR. The third embodiment is also formed as the aforementioned surface plasmon resonance sensor. In the sensor of the third embodiment, the shape of a dielectric block differs from that shown in FIG. 1. That is, a first dielectric block 41 with a square cross section is employed instead of the first dielectric prism 11 employed in the sensor of FIG. 1. In addition, a second dielectric block 51 for compensation, which has a square cross section, is employed according to the shape of the first dielectric block 41.

As with the first embodiment, a light beam L is emitted from a laser light source 16 and is collimated by a collimator lens 17. The collimated light beam L enters the first dielectric block 41 and strikes an interface 11a between the first dielectric block 41 and a metal film 13. The incidence angle θ of the light beam L with respect to the interface 41a is set so that a condition for total internal reflection is satisfied at the interface 41a and so that surface plasmon resonance is able to occur.

The light beam L incident on the interface 41a is totally reflected there. The totally reflected light beam L emerges from the first dielectric block 41. The light beam L emerging from the first dielectric block 41 enters the second dielectric block 51 and is totally reflected at the interface between the second dielectric block 51 and a diffusing film 24. When this is occurring, evanescent light emerges from the interface and is diffused by the diffusing film 24. In this manner, an image carried by the totally reflected light beam L is formed on the diffusing film 24. The picking-up of the image, the measurement of the refractive index distribution of a sample 15 based on the image, etc., are the same as in the first embodiment.

The second dielectric block 51 for compensation is formed from the same material as the first dielectric block 41 and has the same sectional shape as that of the first dielectric block 41 within the incidence plane of the light beam L with respect to the interface 41a. The second dielectric block 51 is disposed so that the light beam L emerging from the first dielectric block 41 enters along the same optical path as the optical path along which the light beam L enters the first dielectric block 41. If the second dielectric block 21 is disposed in this way, compensation for image distortion due to a variation in the optical path can be made. That is, an image that the light beam L carries at the face 51a of the second dielectric block 51 (which corresponds to the interface 41a of the first dielectric block 41) does not contain image distortion due to a variation in the optical path.

Figure 5:
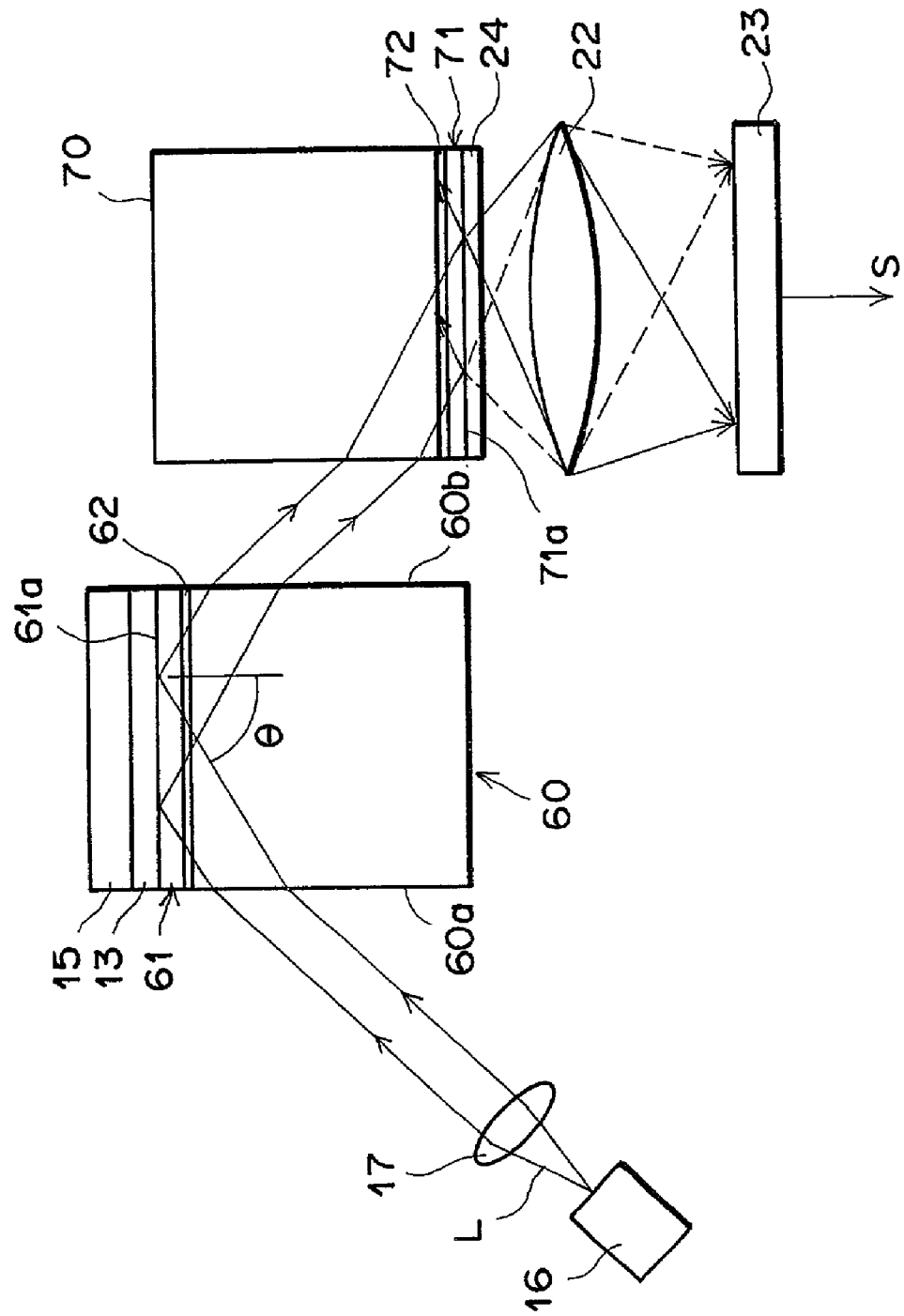
FIG. 5 is a side view showing a surface plasmon resonance sensor constructed according to a fourth embodiment of the present invention.

FIG. 5 shows a fourth embodiment of the present invention utilizing ATR. The fourth embodiment is also formed as the aforementioned surface plasmon resonance sensor. The sensor of the fourth embodiment differs in dielectric block constitution, compared with the sensor shown in FIG. 4. That is, instead of the first dielectric block 41 of FIG. 4, the fourth embodiment employs a first dielectric block 60, and a first dielectric plate 61 mounted on the top face of the first dielectric block 60 through refractive index-matching oil 62. The first dielectric block 60 has a light entrance face 60a and a light exit face 60b. The first dielectric plate 61 has a face that constitutes the interface 61a between the first dielectric plate 61 and a metal film 13.

The fourth embodiment is further provided with a second dielectric block 70 for image distortion compensation, and a second dielectric plate 71 joined with the bottom face of the second dielectric block 70 through refractive index-matching oil 72. A bottom face 71a (which is a face corresponding to the face of the first dielectric plate 61 constituting the interface 61a) of the second dielectric plate 71 is provided with a diffusing film 24.

The picking-up of an image formed by the diffusing film 24, the measurement of the refractive index distribution of a sample 15 based on the image, and compensation for image distortion are performed in the same manner as in the third embodiment.

Figure 6:
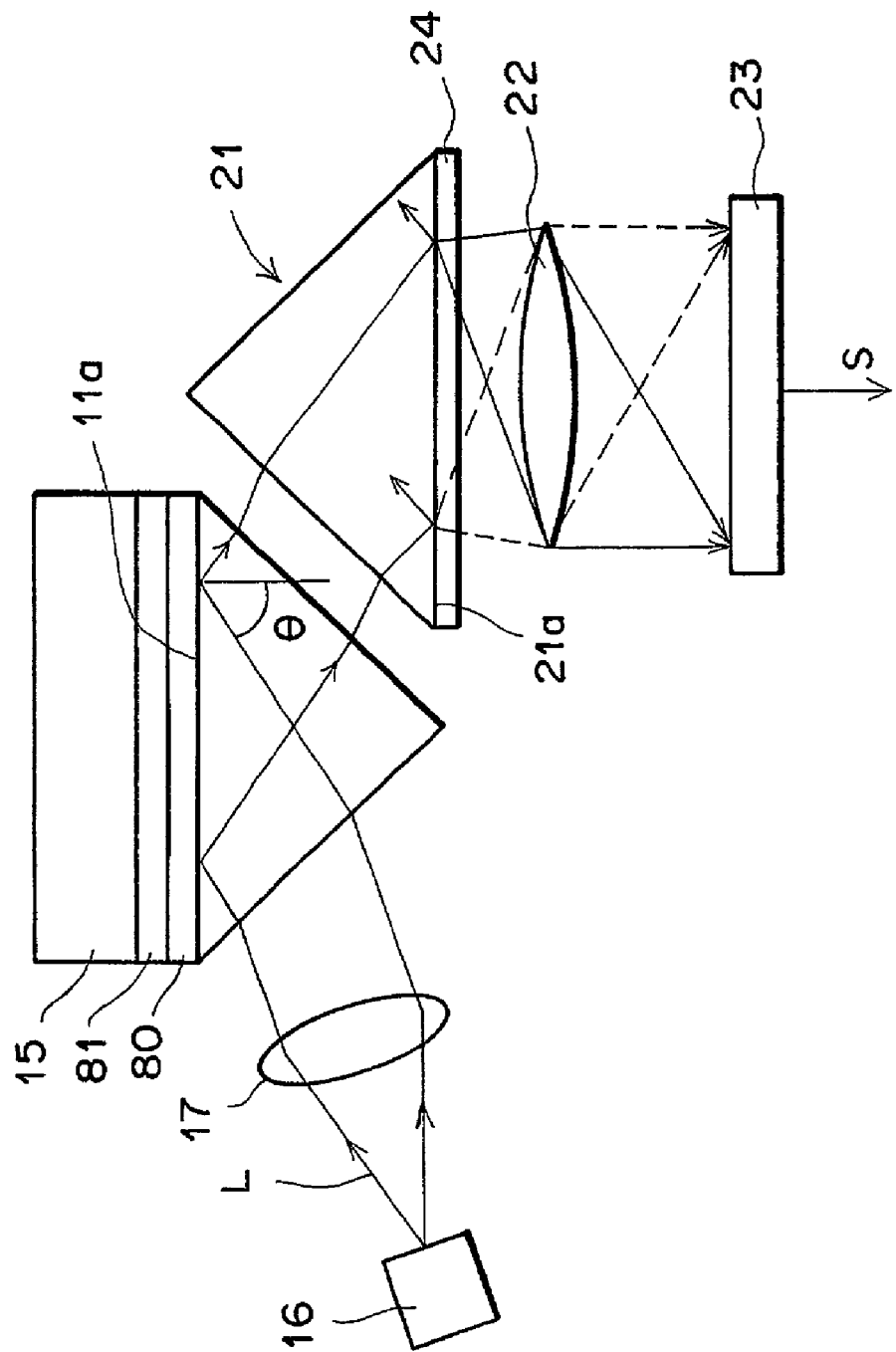
FIG. 6 is a side view showing a leaky mode sensor constructed according to a fifth embodiment of the present invention.

FIG. 6 shows a sensor constructed according to a fifth embodiment of the present invention. The sensor of the fifth embodiment is formed as the aforementioned leaky mode sensor. The sensor of the fifth embodiment is provided with a cladding layer 80 formed on the top face of a first dielectric prism 11, and an optical waveguide layer 81 formed on the cladding layer 80. Other than the above-mentioned points, the fifth embodiment is constructed the same as the first embodiment shown in FIG. 1.

The first dielectric prism 11 in the fifth embodiment is formed, for example, from synthetic resin, or optical glass such as BK7, etc. The cladding layer 80 is formed into the shape of a thin film by employing a dielectric lower in refractive index than the first dielectric prism 11, or a metal such as gold, etc. The optical waveguide layer 81 is formed into a thin film by employing a dielectric higher in refractive index than the cladding layer 80, such as PMMA. The thickness of the cladding layer 80 is 36.5 nm in the case where it is formed from a thin gold film. The thickness of the optical waveguide layer 81 is about 700 nm in the case where it is formed from PMMA.

In the leaky mode sensor of the fifth embodiment, if a light beam L emitted from a laser light 16 strikes the cladding layer 80 through the first dielectric prism 11 at angles of incidence equal to or greater than an angle of total internal reflection, the light beam L is totally reflected at an interface 11a between the first dielectric prism 11 and the cladding layer 80. However, light with a specific wave number, incident on the optical waveguide layer 81 through the cladding layer 80 at a specific incidence angle, propagates through the optical waveguide layer 81 in a waveguide mode. If the waveguide mode is excited in this manner, the greater part of the incident light is confined within the optical waveguide layer 81, and consequently, ATR occurs in which the intensity of light totally reflected at the interface 11a drops sharply.

The wave number of light propagating in the optical waveguide layer 81 depends on the refractive index of the sample 15 on the optical waveguide layer 41. Therefore, as with the aforementioned embodiments, if an image, formed by the diffusing film 24 formed on the face 21a of a second dielectric prism 21, is picked up by a CCD area sensor 23, and the image is reproduced, refractive index distribution in the sample 15 can be measured.

The fifth embodiment is also provided with the second dielectric prism 21 for image distortion compensation. Therefore, the fifth embodiment, as with the first embodiment, is capable of eliminating image distortion that occurs as the incidence angle θ of the light beam L with respect to the interface 11a varies.

While the embodiments for eliminating the aforementioned image distortion have been described, a description will hereinafter be given of embodiments for preventing the aforementioned reduction in accuracy of measurement due to coherent noise.

Figure 7:
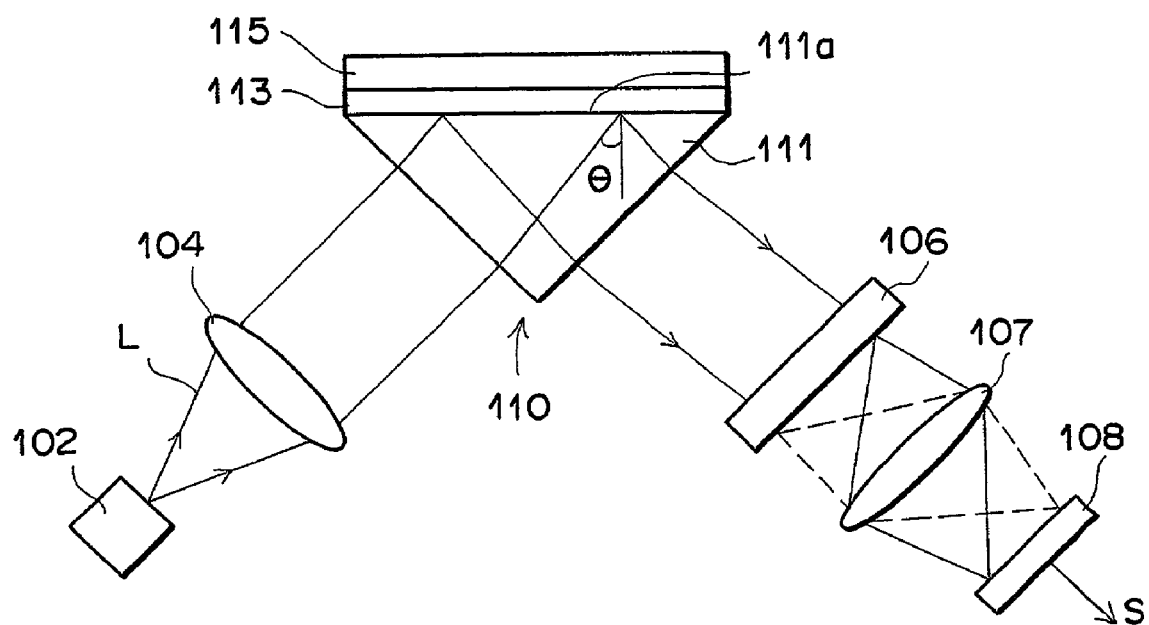
FIG. 7 is a side view showing a surface plasmon resonance sensor constructed according to a sixth embodiment of the present invention.

FIG. 7 shows a sensor utilizing ATR, constructed according to a sixth embodiment of the present invention. The sensor of the sixth embodiment is formed as the aforementioned surface plasmon resonance sensor. In the sensor of the sixth embodiment, a measuring unit 110 has a transparent dielectric block 111 and a metal film 113. The dielectric block 111 is formed from synthetic resin such as polymethylmethacrylate (PMMA), etc., or optical glass such as BK7, etc., and is formed, for example, into the shape of a trigonal prism. The metal film 113 is mounted on the top face of the dielectric block 11, and is formed, for example, from gold, silver, copper, aluminum, etc. A sample 115 to be analyzed is disposed on the metal film 113.

The surface plasmon resonance sensor is provided with a laser light source 102 for emitting a light beam L; a collimator lens 104 for making the divergently emitted light beam L enter an entrance face of the prism 111 as a parallel light beam having a cross section of considerable size; and a screen 106, disposed in the optical path of the parallel light beam emitted from the exit face of the prism 111, and consisting of a diffusing plate for visually imaging the light intensity distribution of the cross section of the parallel light beam L. The surface plasmon resonance sensor is further provided with a CCD area sensor 108 which is a two-dimensional sensor on which the visual image on the screen 106 is formed; and an image forming lens 107 for forming the visual image on the screen 106 onto the CCD area sensor 108.

Operation of the surface plasmon resonance sensor will hereinafter be described. The light beam L emitted from the laser light source 102 is collimated by the collimator lens 104 and has a cross section of considerable size. The collimated light beam L enters the dielectric prism 111 at an entrance face thereof and strikes an interface 111a between the dielectric prism 111 and the metal film 113 at a predetermined incidence angle θ. The incidence angle θ of the light beam L with respect to the interface 111a is set so that a condition for total internal reflection is satisfied at the interface 111a, and so that when a specific substance in the sample 115 is present on the metal film 113, ATR due to surface plasmon resonance is detected.

As previously stated, in order to excite surface plasmon resonance, it is necessary that the light beam L be p-polarized before it strikes the interface 111a. For this reason, the laser light source 102 is disposed so that the polarization direction thereof becomes a predetermined direction. Alternatively, the polarization direction of the light beam L may be controlled with a wavelength plate, a polarizing plate, etc.

The light beam L incident on the interface 111a is totally reflected there. The totally reflected light beam L emerges from the dielectric prism 111, and the light intensity distribution of the cross section of the light beam L is visually imaged onto the screen 106. The image, which is visually formed and diffused at the screen 106, is formed onto the pick-up face of the CCD area sensor 108 by the image forming lens 107. Since the light beam L is visually formed and diffused at the screen 106, an image with a good S/N ratio can be obtained on the CCD area sensor 108 without producing coherent noise that results from laser light.

When the light beam L is totally reflected at the interface 111a, as described above, evanescent waves propagate from the interface 111a to the side of the metal film 113. When the light beam L strikes a point on the interface 111a where a specific substance in the sample 115 is present on the metal film 113, the evanescent waves resonate with the surface plasmon excited at the face of the metal film 113, and consequently, the intensity I of the reflected light is sharply attenuated. That is, in the sixth embodiment, if the light beam L strikes the interface 111a at a predetermined incidence angle at which surface plasmon resonance occurs when a specific substance in the sample 115 is present on the metal film 113, ATR due to surface plasmon resonance is observed at a point where a specific substance in the sample 115 is present on the metal film 113. Therefore, the two-dimensional distribution of specific substances in the sample 115 can be observed. Furthermore, the distribution of substances where an angle above or below the specific incidence angle $\theta_{sp}$ is an angle at which ATR occurs, that is, the two-dimensional physical properties of a sample, such as the refractive index distribution of a sample, can be detected. For instance, if a sample, such as a gel sheet employed in electrophoresis, is placed on the metal film 113 and measured, the two-dimensional physical-property information on specific substances (substances to be analyzed) distributed in the sample can be obtained.

Note that if an image signal S output from the CCD area sensor 108 is input to an image display means such as a CRT display, a liquid crystal display panel, etc., and an image carried by the image signal S is reproduced and displayed, the two-dimensional physical properties in the sample 115 can be observed. In addition, if the image signal S is input to an optical scanning-recording unit, etc., an image carried by the image signal S can be reproduced as a hard copy. Note that instead of the screen 106 consisting of a diffuser, a screen consisting of a phosphor, etc., may be employed.

Figure 8:
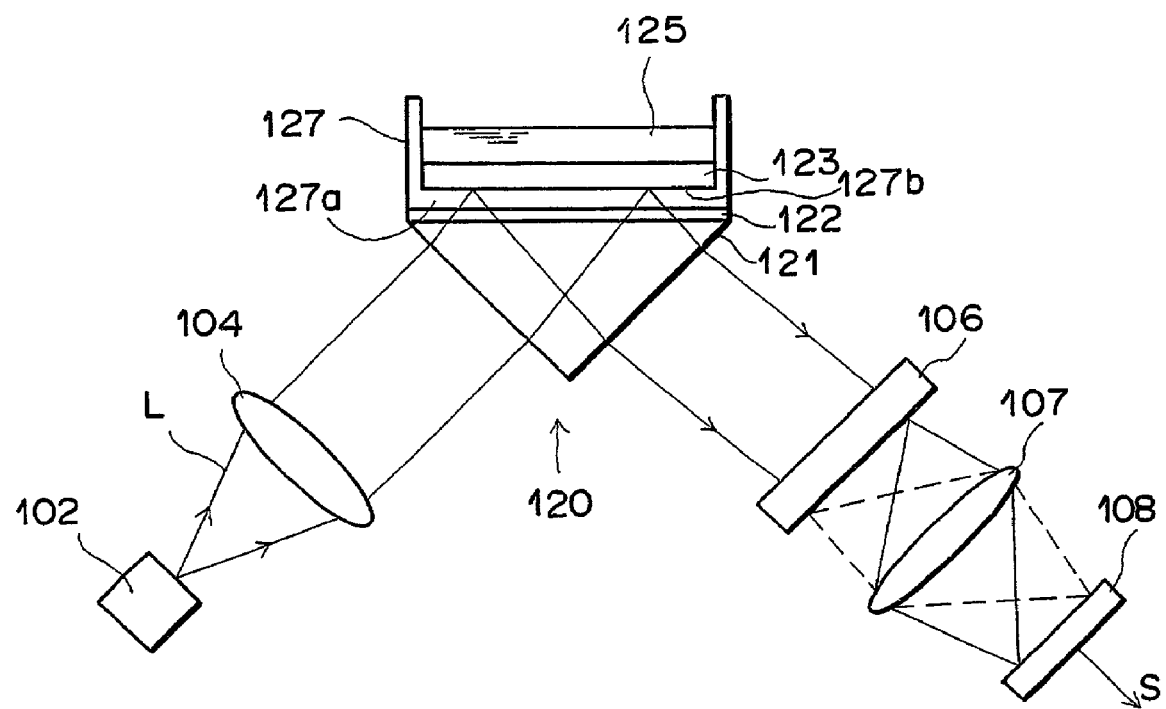
FIG. 8 is a side view showing a surface plasmon resonance sensor constructed according to a seventh embodiment of the present invention.

FIG. 8 shows a sensor utilizing ATR, constructed according to a seventh embodiment of the present invention. The sensor of the seventh embodiment is also formed as the aforementioned surface plasmon resonance sensor. In the sensor of the seventh embodiment, a measuring unit 120 differs in shape from that shown in FIG. 7. The measuring unit 120 in the seventh embodiment consists of a dielectric prism 121 and a container 127 having a liquid-holding portion for holding a liquid sample 125. The bottom portion 127a of the container 127 has the same refractive index as that of the prism 121. The prism 121 and the container 127 are joined together through a refractive index-matching means 122. A metal film 123 is disposed on the bottom portion 127a, and the liquid sample 125 is held on the metal film 123 by the container 127. Note that when the liquid sample 125 is exchanged for a new one, the container 127 is exchanged for a new one.

Light beam L collimated by a collimator lens 104 enters the dielectric prism 121 at the entrance face thereof and strikes a predetermined region (corresponding to the cross section of the light beam) on the interface 127b between the bottom portion 127a of the container 127 and the metal film 123 through the index-matching means 122 and the bottom portion 127a. The light beam L is reflected at the interface 127b and emerges from the exit face of the prism 121. Next, the light intensity distribution of the cross section of the reflected light beam L is visually imaged onto the screen 106 disposed in the optical path of the reflected light beam L. The picking-up of the image, the measurement of the refractive index distribution of the sample 125 based on the image, etc., are the same as in the sixth embodiment.

FIG. 9 shows a sensor utilizing ATR, constructed according to an eighth embodiment of the present invention. The sensor of the eighth embodiment is also formed as the aforementioned surface plasmon resonance sensor. In the sensor of the eighth embodiment, a measuring unit 130 differs in shape from that shown in FIG. 7. The measuring unit 130 in the eighth embodiment has a dielectric prism 131; a metal film 113, formed on the top face of the dielectric prism 131, which consists of gold, silver, copper, aluminum, etc.; a plurality of different sensing media 134a, 134b, . . . disposed on different points on the metal film 133; and a sample holding portion 137 with a passage through which a liquid sample 135 passes while contacting the sensing media 134a, 134b, . . . .

The sensing media 134a, 134b, . . . interact with different specific substances, respectively. As a combination of each specific substance and the sensing medium, there is, for example, a combination of an antigen and an antibody. That is, the eighth embodiment disposes a plurality of different sensing media 134a, 134b, . . . and is able to inspect whether or not specific substances interacting with the sensing media 134a, 134b, . . . are present in the sample 135.

In measuring the liquid sample 135, the sensing media react with the specific substances in the sample, so that there is a problem that the density of the sample will vary. However, in the eighth embodiment, the liquid sample 135 passes through the sample holding portion 137 while contacting the sensing media 134a, 134b, . . . . In this manner, a variation in the density of the liquid sample 135 is prevented and the density of the liquid sample 135 is always kept constant. That is, measurements can always be made under the same condition.

The light beam L, which strikes an interface 131a between the prism 131 and the metal film 133, has such a cross section that can irradiate the different sensing media 134a, 134b, . . . disposed on different points on the metal film 133. The light intensity distribution of the cross section of the light beam L reflected at the interface 131a is visually imaged onto a screen 106, and is picked up by a CCD area sensor 108. Based on the light intensities at the points on the CCD area sensor 108 which correspond to the sensing media 134a, 134b, . . . , the densities, etc., of specific substances in the liquid sample 135 can be detected.

FIG. 10 shows a sensor utilizing ATR, constructed according to a ninth embodiment of the present invention. The sensor of the ninth embodiment is also formed as the aforementioned surface plasmon resonance sensor. In the sensor of the ninth embodiment, a measuring unit 140 differs in shape from that shown in FIG. 7. The measuring unit 140 in the ninth embodiment has a dielectric block 141 and a metal film 143. The dielectric block 141 is formed, for example, into the shape of a generally quadrangular pyramid, a lower portion thereof being cut out. The dielectric block 141 consists of a first portion through which a light beam L passes, and a second container portion 141a for holding a liquid sample 145, both portions being formed integrally with each other. The metal film 143 is provided on the bottom face of the container portion 141a of the dielectric block 141, and is formed from gold, silver, copper, aluminum, etc. A sensing medium 144 is mounted on the metal film 143.

A light beam L emitted from a laser light source 102 and is collimated by a collimator lens 104. The collimated light beam L enters the dielectric block 141 at the entrance face and strikes an interface 141b between the dielectric block 141 and the metal film 143. The incidence angle θ of the light beam L with respect to the interface 141b is set so that a condition for total internal reflection is satisfied at the interface 141b and that surface plasmon resonance can occur.

The light beam L incident on the interface 141b is totally reflected there. The totally reflected light beam L emerges from the exit face of the dielectric block 141. The light intensity distribution of the cross section of the light beam L is visually imaged onto a screen 106 and is diffused by the screen 106 that is a diffusing plate.

The picking-up of the image on the screen 105, the measurement of the two-dimensional physical properties of a sample 145 based on the image, etc., are the same as in the seventh embodiment.

In the ninth embodiment, the refractive index of the sensing medium 144 varies with the coupled state between a specific substance in a sample 145 and the sensing medium 144. Therefore, if the light intensity distribution of the cross section of the light beam L reflected at the interface 141b is picked up by a CCD area sensor 108, and the image is utilized, the refractive index distribution of the sensing medium 144, that is, the distribution of coupled states between a specific substance in the sample 145 and the sensing medium 144 can be obtained.

Figure 11:
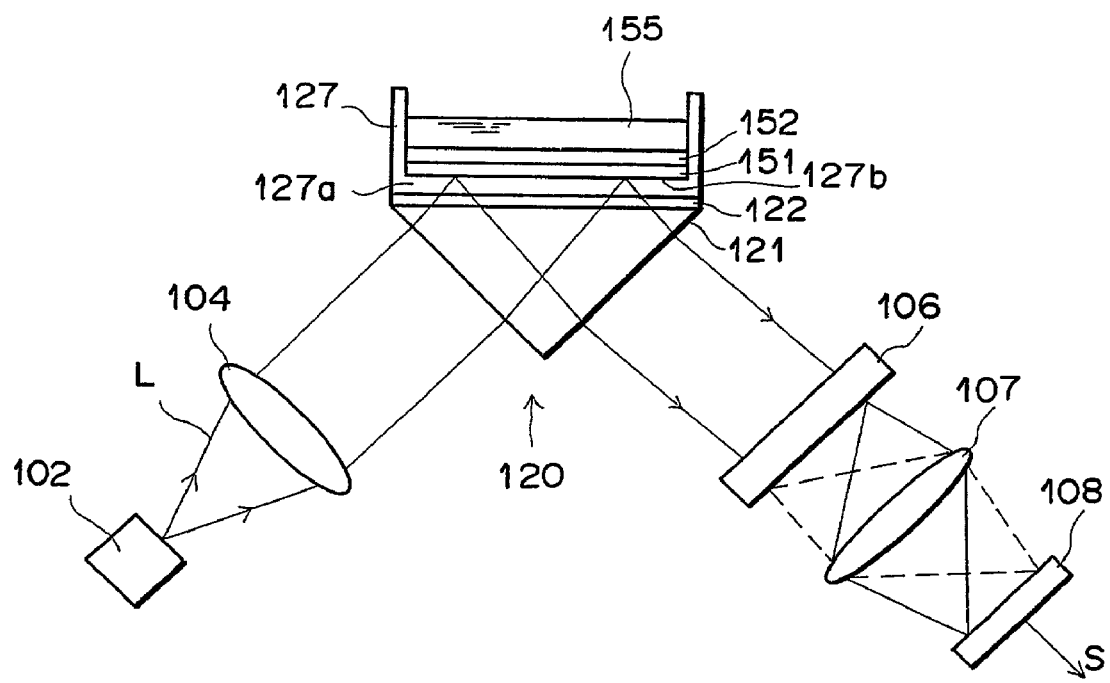
FIG. 11 is a side view showing a leaky mode sensor constructed according to a tenth embodiment of the present invention.

FIG. 11 shows a sensor utilizing ATR, constructed according to a tenth embodiment of the present invention. The sensor of the tenth embodiment is formed as the aforementioned leaky mode sensor. A measuring unit 120' in the tenth embodiment consists of a dielectric prism 121 and a container 127 having a liquid-holding portion for holding a liquid sample 155. The bottom portion 127a of the container 127 has the same refractive index as that of the prism 121. The prism 121 and the container 127 are joined together through index-matching means 122. A cladding layer 151 is disposed on the side of the liquid-holding portion of the bottom portion 127a of the container 127, and an optical waveguide layer 152 is formed on the cladding layer 151. The liquid sample 155 is held on the optical waveguide layer 152 by the container 127. Thus, the tenth embodiment differs from the seventh embodiment in that instead of a metal film, the cladding layer 151 and the optical waveguide layer 152 are employed. Other than that, the tenth embodiment is constructed the same as the seventh embodiment.

The dielectric prism 121 in the tenth embodiment is formed, for example, from synthetic resin, or optical glass such as BK7, etc. The cladding layer 151 is formed into the shape of a thin film by employing a dielectric lower in refractive index than the dielectric prism 121, or metal such as gold, etc. The optical waveguide layer 152 is also formed into a thin film by employing a dielectric higher in refractive index than the cladding layer 151, such as PMMA. The thickness of the cladding layer 151 is 36.5 nm in the case where it is formed from a thin gold film. The thickness of the optical waveguide layer 152 is about 700 nm in the case where it is formed from PMMA.

In the leaky mode sensor of the tenth embodiment, if a light beam L emitted from the laser light 102 passes through the dielectric prism 121, the refractive index-matching means 122, and the bottom portion 127a of the container 127 and then strikes a predetermined region on the interface 127b between the bottom portion 127a and the cladding layer 151 at an incidence angle equal to or greater than an angle of total internal reflection, the light beam L is totally reflected at the interface 127b. However, light with a specific wave number, incident on the optical waveguide layer 152 through the cladding layer 151 at a specific incidence angle, propagates through the optical waveguide layer 152 in a waveguide mode. If the waveguide mode is excited in this manner, the greater part of the incident light is confined within the optical waveguide layer 152, and consequently, ATR occurs in which the intensity of light totally reflected at the interface 127b drops sharply.

The wave number of light propagating in the optical waveguide layer 152 depends on the refractive index of the sample 155 on the optical waveguide layer 152. Therefore, as with the aforementioned embodiments, if an image carried by the light intensity distribution of the cross section of the light reflected at the interface 127b is picked up by a CCD area sensor 108, and the image is reproduced, refractive index distribution in the sample 155 can be measured.

In addition, as with the aforementioned embodiments, the light intensity distribution of the cross section of the reflected light is visually formed as an image and diffused at the screen 106, and the diffused image is formed onto the CCD area sensor 108. Therefore, the tenth embodiment is capable of making an accurate measurement, while preventing coherent noise that results from laser light.

Finally, while the present invention has been described with reference to the preferred embodiments thereof, the invention is not to be limited to the details given herein, but may be modified within the scope of the invention hereinafter claimed.

What is claimed is:

1. A sensor utilizing attenuated total reflection, comprising:
    a first dielectric block;
    a thin film layer, formed on a first face of said dielectric block, for placing a sample thereon;
    a light source for emitting a light beam;
    an optical incidence system for collimating said light beam, and making the collimated light beam enter said dielectric block at a predetermined incidence angle so that a condition for total internal reflection is satisfied at an interface between said dielectric block and said thin film layer; and
    photodetection means for detecting the refractive index distribution of said sample that is obtained within a plane along said interface, by detecting an image carried by the light beam totally reflected at said interface;
    wherein an optical compensation system for compensating for image distortion which is produced by said dielectric block when said predetermined incidence angle of said light beam varies is provided.

2. The sensor as set forth in claim 1, wherein said optical compensation system comprises:
    a second dielectric block for compensation, having the same cross section as that of said first dielectric block within an incidence plane of said light beam with respect to said interface, also being formed from a material of the same refractive index as said first dielectric block, and being disposed so that it receives the light beam emerging from said first dielectric block; and
    a screen for image observation, formed on a face of said second dielectric block that corresponds to said first face of said first dielectric block.

3. The sensor as set forth in claim 2, wherein said screen is composed of diffusers.

4. The sensor as set forth in claim 2, wherein said screen is composed of phosphors.

5. The sensor as set forth in claim 1, wherein said first dielectric block is formed as a single block having said first face on which said thin film layer is formed, a second face that said light beam enters, and a third face from which said light beam emerges.

6. The sensor as set forth in claim 1, wherein
    said first dielectric block comprises a first portion having a second face that said light beam enters and a third face from which said light beam emerges, and a second portion having said first face on which said thin film layer is formed; and
    said first portion and said second portion are joined together through a refractive index-matching means.

7. The sensor as set forth in claim 1, wherein said optical compensation system comprises:
    a second dielectric block having a same cross section as that of said first dielectric block within an incidence plane of said light beam with respect to said interface, said second dielectric block being formed from a material of the same refractive index as said first dielectric block, and being disposed so that it receives a light beam emerging from said first dielectric block.

8. A sensor utilizing attenuated total reflection that occurs due to surface plasmon resonance, comprising:
    a first dielectric block;
    a thin film layer comprising a metal film, formed on a first face of said dielectric block, for placing a sample thereon;
    a light source for emitting a light beam;
    an optical incidence system for collimating said light beam, and making the collimated light beam enter said dielectric block at a predetermined incidence angle so that a condition for total internal reflection is satisfied at an interface between said dielectric block and said thin film layer; and
    photodetection means for detecting the refractive index distribution of said sample that is obtained within a plane along said interface, by detecting an image carried by the light beam totally reflected at said interface;
    wherein an optical compensation system for compensating for image distortion which is produced by said dielectric block when said predetermined incidence angle of said light beam varies.

9. The sensor as set forth in claim 8, wherein said optical compensation system comprises:
    a second dielectric block for compensation, having the same cross section as that of said first dielectric block within an incidence plane of said light beam with respect to said interface, also being formed from a material of the same refractive index as said first dielectric block, and being disposed so that it receives the light beam emerging from said first dielectric block; and
    a screen for image observation, formed on a face of said second dielectric block that corresponds to said first face of said first dielectric block.

10. The sensor as set forth in claim 9, wherein said screen is composed of diffusers.

11. The sensor as set forth in claim 9, wherein said screen is composed of phosphors.

12. The sensor as set forth in claim 8, wherein said first dielectric block is formed as a single block having said first face on which said thin film layer is formed, a second face that said light beam enters, and a third face from which said light beam emerges.

13. The sensor as set forth in claim 8, wherein
    said first dielectric block comprises a first portion having a second face that said light beam enters and a third face from which said light beam emerges, and a second portion having said first face on which said thin film layer is formed; and
    said first portion and said second portion are joined together through a refractive index-matching means.

14. A sensor utilizing attenuated total reflection which occurs when a waveguide mode in an optical waveguide layer is excited, comprising:
    a first dielectric block;
    a thin film layer comprising (1) a cladding layer formed on a first face of said dielectric block and (2) said optical waveguide layer formed on said cladding layer;

a light source for emitting a light beam;

an optical incidence system for collimating said light beam, and making the collimated light beam enter said dielectric block at a predetermined incidence angle so that a condition for total internal reflection is satisfied at an interface between said dielectric block and said cladding layer; and photodetection means for detecting the refractive index distribution of said sample that is obtained within a plane along said interface, by detecting an image carried by the light beam totally reflected at said interface;

wherein an optical compensation system for compensating for image distortion which is produced by said dielectric block when said predetermined incidence angle of said light beam varies.

15. The sensor as set forth in claim 14, wherein said optical compensation system comprises:

a second dielectric block for compensation, having the same section as that of said first dielectric block within an incidence plane of said light beam with respect to said interface, also being formed from a material of the same refractive index as said first dielectric block, and being disposed so that it receives the light beam emerging from said first dielectric block; and a screen for image observation, formed on a face of said second dielectric block that corresponds to said first face of said first dielectric block.

16. The sensor as set forth in claim 15, wherein said screen is composed of diffusers.

17. The sensor as set forth in claim 15, wherein said screen is composed of phosphors.

18. The sensor as set forth in claim 14, wherein said first dielectric block is formed as a single block having said first face on which said thin film layer is formed, a second face that said light beam enters, and a third face from which said light beam emerges.

19. The sensor as set forth in claim 14, wherein said first dielectric block comprises a first portion having a second face that said light beam enters and a third face from which said light beam emerges, and a second portion having said first face on which said thin film layer is formed; and said first portion and said second portion are joined together through a refractive index-matching means.

20. A sensor utilizing attenuated total reflection, comprising:

a light source for emitting a light beam;

a measuring unit comprising (1) a dielectric block transparent to said light beam, (2) a thin film layer formed on a first face of said dielectric block, and (3) a sample holding mechanism for holing a sample on said thin film layer;

an optical incidence system for collimating said light beam so that said light beam has a cross section of considerable size, and making the collimated light beam enter said dielectric block at a predetermined incidence angle so that a condition for total internal reflection is satisfied at an interface between said dielectric block and said thin film layer;

a screen, disposed in an optical path of the collimated light beam totally reflected at said interface, for converting light intensity distribution in the cross section of said collimated light beam into a visual image;

a two-dimensional sensor on which said visual image on said screen is formed; and an optical image-forming system for forming said visual image on said screen onto said two-dimensional sensor.

21. The sensor as set forth in claim 20, wherein said screen comprises a diffusing plate.

22. The sensor as set forth in claim 20, wherein said screen comprises a fluorescent plate.

23. The sensor as set forth in claim 20, wherein a sensing medium that interacts with a specific component in said sample is disposed on said thin film layer.

24. The sensor as set forth in claim 23, wherein said sample holding mechanism is provided with a passage through which a liquid sample passes while contacting said sensing medium.

25. The sensor as set forth in claim 20, wherein said sample holding mechanism is formed into the shape of a container having a liquid-holding portion for holding a liquid sample.

26. The sensor as set forth in claim 20, wherein said dielectric block comprises a first portion having a second face that said light beam enters and a third face from which said light beam emerges, and a second portion formed separately from said first portion and having said first face on which said thin film layer is formed;

said second portion and said sample holding mechanism are formed integrally with each other; and said second portion is joined with said first portion through a refractive index-matching means.

27. The sensor as set forth in claim 20, wherein said dielectric block, thin film layer, and sample holding mechanism of said measuring unit are formed integrally with one another.

28. A sensor utilizing attenuated total reflection that occurs due to surface plasmon resonance, comprising:

a light source for emitting a light beam;

a measuring unit comprising (1) a dielectric block transparent to said light beam, (2) a thin film layer comprising a metal film, formed on a first face of said dielectric block, and (3) a sample holding mechanism for holing a sample on said thin film layer;

an optical incidence system for collimating said light beam so that said light beam has a cross section of considerable size, and making the collimated light beam enter said dielectric block at a predetermined incidence angle so that a condition for total internal reflection is satisfied at an interface between said dielectric block and said thin film layer;

a screen, disposed in an optical path of the collimated light beam totally reflected at said interface, for converting light intensity distribution in the cross section of said collimated light beam into a visual image;

a two-dimensional sensor on which said visual image on said screen is formed; and an optical image-forming system for forming said visual image on said screen onto said two-dimensional sensor.

29. The sensor as set forth in claim 28, wherein said screen comprises a diffusing plate.

30. The sensor as set forth in claim 28, wherein said screen comprises a fluorescent plate.

31. The sensor as set forth in claim 28, wherein a sensing medium that interacts with a specific component in said sample is disposed on said thin film layer.

32. The sensor as set forth in claim 31, wherein said sample holding mechanism is provided with a passage through which a liquid sample passes while contacting said sensing medium.

33. The sensor as set forth in claim 28, wherein said sample holding mechanism is formed into the shape of a container having a liquid-holding portion for holding a liquid sample.

34. The sensor as set forth in claim 28, wherein
said dielectric block comprises a first portion having a second face that said light beam enters and a third face from which said light beam emerges, and a second portion formed separately from said first portion and having said first face on which said thin film layer is formed;
said second portion and said sample holding mechanism are formed integrally with each other; and
said second portion is joined with said first portion through a refractive index-matching means.

35. The sensor as set forth in claim 28, wherein said dielectric block, thin film layer, and sample holding mechanism of said measuring unit are formed integrally with one another.

36. A sensor utilizing attenuated total reflection that occurs when a waveguide mode in an optical waveguide layer is excited, comprising:
a light source for emitting a light beam;
a measuring unit comprising (1) a dielectric block transparent to said light beam, (2) a thin film layer comprising a cladding layer formed on a first face of said dielectric block, and said optical waveguide layer formed on said cladding layer, and (3) a sample holding mechanism for holing a sample on said thin film layer;
an optical incidence system for collimating said light beam so that said light beam has a cross section of considerable size, and making the collimated light beam enter said dielectric block at a predetermined incidence angle so that a condition for total internal reflection is satisfied at an interface between said dielectric block and said thin film layer;
a screen, disposed in an optical path of the collimated light beam totally reflected at said interface, for converting light intensity distribution in the cross section of said collimated light beam into a visual image;
a two-dimensional sensor on which said visual image on said screen is formed; and
an optical image-forming system for forming said visual image on said screen onto said two-dimensional sensor.

37. The sensor as set forth in claim 36, wherein said screen comprises a diffusing plate.

38. The sensor as set forth in claim 36, wherein said screen comprises a fluorescent plate.

39. The sensor as set forth in claim 36, wherein a sensing medium that interacts with a specific component in said sample is disposed on said thin film layer.

40. The sensor as set forth in claim 39, wherein said sample holding mechanism is provided with a passage through which a liquid sample passes while contacting said sensing medium.

41. The sensor as set forth in claim 36, wherein said sample holding mechanism is formed into the shape of a container having a liquid-holding portion for holding a liquid sample.

42. The sensor as set forth in claim 36, wherein
said dielectric block comprises a first portion having a second face that said light beam enters and a third face from which said light beam emerges, and a second portion formed separately from said first portion and having said first face on which said thin film layer is formed;
said second portion and said sample holding mechanism are formed integrally with each other; and
said second portion is joined with said first portion through a refractive index-matching means.

43. The sensor as set forth in claim 36, wherein said dielectric block, thin film layer, and sample holding mechanism of said measuring unit are formed integrally with one another.

* * * * *